United States Patent [19]

Fink

[11] Patent Number: 5,752,607

[45] Date of Patent: May 19, 1998

[54] PROCESS FOR DISTINGUISHING PLUMBING PARTS BY THE COATINGS APPLIED THERETO

[75] Inventor: Klaus Fink, Northfield, Ohio

[73] Assignee: Moen Incorporated, North Olmsted, Ohio

[21] Appl. No.: 617,079

[22] Filed: Mar. 18, 1996

[51] Int. Cl.[6] ................................................ B07C 5/00
[52] U.S. Cl. ................................. 209/576; 209/578
[58] Field of Search ................................ 209/576, 577, 209/579, 587, 578, 558, DIG. 938; 250/339.01, 341, 226, 223 B; 356/239, 240, 402

[56] References Cited

U.S. PATENT DOCUMENTS

| | | |
|---|---|---|
| 2,798,605 | 7/1957 | Richards. |
| 3,721,501 | 3/1973 | Atkinson et al.. |
| 4,017,194 | 4/1977 | Conroy et al.. |
| 4,204,950 | 5/1980 | Burford ............................ 209/558 |
| 4,227,083 | 10/1980 | Sherinski. |
| 4,254,337 | 3/1981 | Yasujima et al.. |
| 4,558,786 | 12/1985 | Lane ................................. 209/558 |
| 5,206,510 | 4/1993 | Wolf et al.. |
| 5,318,172 | 6/1994 | Kenny et al.. |

Primary Examiner—Robert J. Oberleitner
Assistant Examiner—C. T. Bartz
Attorney, Agent, or Firm—Dorn, McEachran, Jambor & Keating

[57] ABSTRACT

A process to distinguish plumbing parts, either individually or as combined into a plumbing product, in which one of two types of coatings have been applied to the parts, with the parts being visually indistinguishable by the type of coating. The parts are illuminated with a non-visible light operating at a frequency which will be absorbed by only one type of coating. The parts may be coated with an essentially organic coating or an essentially inorganic coating. Only one of these coatings will absorb the non-visible light and such absorption will be displayed so as to distinguish between parts having the different types of coatings.

10 Claims, 1 Drawing Sheet

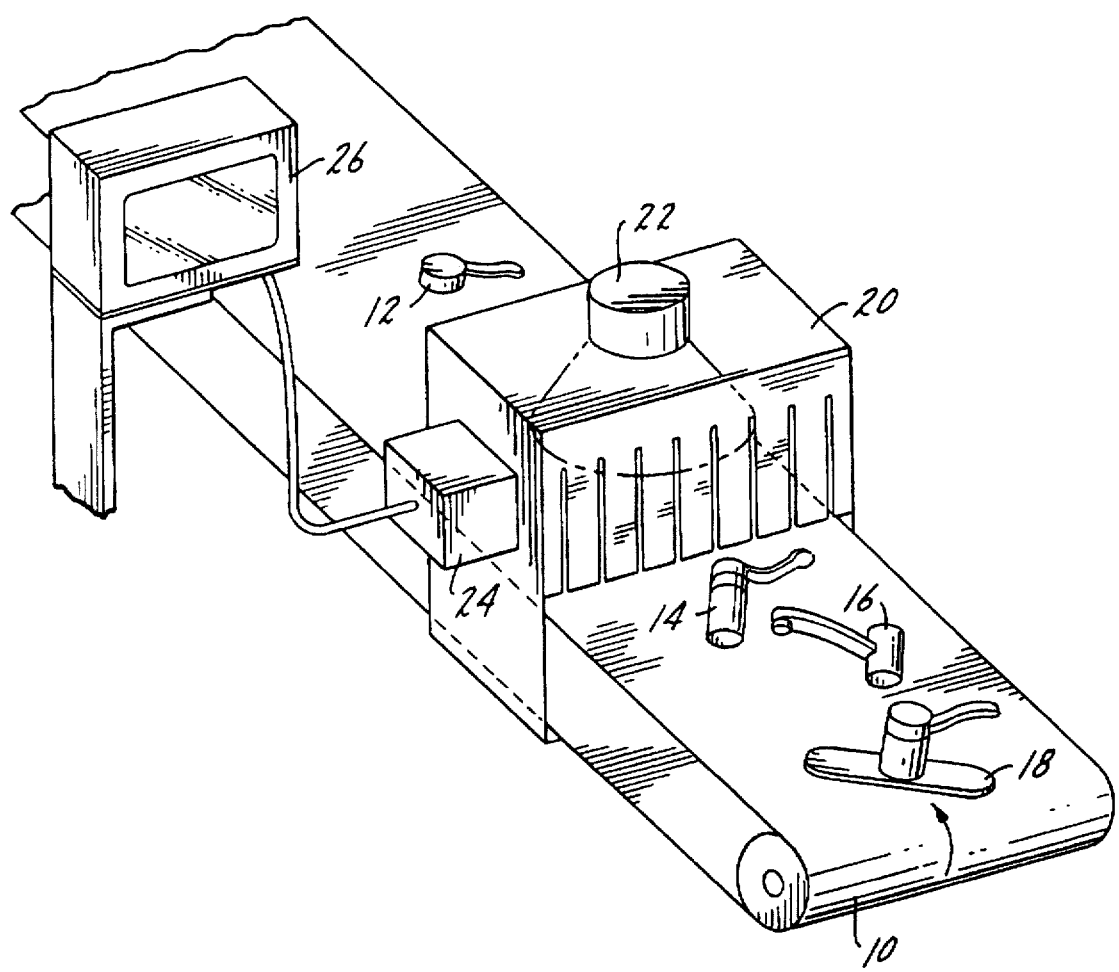

5,752,607

PROCESS FOR DISTINGUISHING PLUMBING PARTS BY THE COATINGS APPLIED THERETO

THE FIELD OF THE INVENTION

It has been the practice in the manufacture of plumbing products, such as faucet housings, tub spouts, shower heads and the like, to use an essentially organic coating such as a polymer as the final exterior protective film for a brass plated product. Unfortunately, such a polymer coating will often degrade in service, with the end result that the brass beneath the polymer coating may corrode and the plumbing part may no longer be considered acceptable by the customer.

The plumbing industry is moving toward the use of inorganic coatings as a way to provide long lasting finishes. However, not all plumbing parts will receive an inorganic coating which creates the problem of distinguishing between parts having an inorganic coating and parts having an organic coating when the parts are visually indistinguishable. Since the plumbing parts mentioned will often have a number of exterior components which go to make up the final product, it is absolutely necessary that parts with similar coatings be used in the assembly of the final plumbing product. The present invention provides a process or method for distinguishing plumbing parts, according to the type of coating, when the parts themselves are visually indistinguishable. Specifically, the plumbing parts, either individually or after assembly, will be illuminated by a non-visible light source, for example in the ultraviolet spectrum or in the infrared spectrum, which non-visible light has a frequency or wave length which will cause the light to be absorbed by the organic coating, but not to be absorbed by an inorganic coating. The parts so illuminated, and conventionally this will be done in a closed environment such as a black box, will be visually displayed via a detector and optics on an associated viewer or screen so that employees watching the parts move down an assembly line can quickly remove or separate parts according to the type of coating which is applied thereto.

The organic coating, which is a polymer, may be a polyurethane, an acrylic, an epoxy, or a similar chemical composition. A useful inorganic coating is zirconium carbonitride which has the advantage that it has the appearance of brass.

SUMMARY OF THE INVENTION

The present invention relates to a process for distinguishing plumbing parts on the basis of the coating applied thereto through the use of a non-visible light source which is absorbed by one coating and not the other.

A primary purpose of the invention is a simple, fast, reliable process for distinguishing between plumbing parts having differing coatings, when to the eye the coatings appear to be identical in color.

Another purpose is a process of the type described which can distinguish between inorganic and organic coatings on plumbing parts or similar products and utilizes non-visible light in a spectrum which will be absorbed by cone coating and not the other.

Another purpose is a process of the type described which utilizes ultraviolet light having a 200–300 nanometer wave length, which non-visible light will be absorbed by the polymer coating and not by a ceramic coating.

Another purpose is a process of the type described which utilizes infrared light having a ware length of approximately 3 to 6 microns, which non-visible light will be absorbed by the polymer coating and not by a ceramic coating.

Other purposes will appear in the ensuing specification, drawing and claims.

BRIEF DESCRIPTION OF THE DRAWINGS

The invention is illustrated diagrammatically in the attached drawing which is a diagrammatic illustration of the process disclosed herein.

DESCRIPTION OF THE PREFERRED EMBODIMENT

In the manufacture of plumbing parts which are to have the appearance of brass, the common practice has been to first electroplate a coating of brass, and then to apply a coating of an organic polymer such as polyurethane or acrylic or epoxy. The polymer coating does not have the desired wear resistant characteristics and particularly if certain types of cleaning agents are used in the area of the sink around such a brass plumbing part, for example a faucet, the coating will degrade and the brass plating will then be subject to corrosion. To overcome this problem, the plumbing industry has begun to coat plumbing parts such as faucets, tub spouts, shower heads and the like, with alternate coatings. Zirconium carbo-nitride has the advantage that it has the appearance of trass, therefore eliminating the chrome removal step.

However, the use of two different types of coatings on plumbing parts which are visually indistinguishable presents problems in the assembly of the final plumbing product. It is essential that all of the parts for a particular plumbing product have the same type of exterior coating. Since the parts may be visually indistinguishable, what is required is a simple, reliable process for quickly determining the type of coating on plumbing parts which have an identical outer appearance.

The present invention utilizes light in the non-visible spectrum to illuminate all plumbing parts moving on a conveyor system. Light in this spectrum will be absorbed by a polymer, but not by an inorganic coating. A detector may be positioned adjacent the illuminating light and the detector, preferably via a video screen, will give a visual indication to a workman as to the type of coating on a particular part. Preferably, ultraviolet light having a wave length of 200–300 nanometer is utilized. However, infrared light can also be used. Experimental data shows that infrared light having a wave length of approximately 3 to 6 microns will be absorbed by epoxy and acrylic polymer coatings. Such light will be absorbed by a polymer, but not by a ceramic, because light of the described wave length provides excitation of the carbon hydrogen bonds in the polymer. The light may be provided by a laser diode or by a broad spectrum ultraviolet lamp plus optics which allows illumination in the described wave length.

In the drawing, a conveyor is indicated at 10 and as shown carries a plurality of different types of plumbing parts. There is a faucet handle 12, a second type of faucet handle 14, a faucet spout 16, and an assembled faucet 18. The invention is applicable to any type of plumbing part or any type of process in which it is necessary to distinguish between coatings applied to similar products.

Extending over the top of the conveyor 10 is an enclosure 20 which has a lamp 22. The lamp 22 may provide light in a broad spectrum, including the ultraviolet spectrum. In the alternative, a laser diode providing a light of a very specific wave length may be utilized. What is important is to provide illumination within the enclosure 22 of a specific frequency or wave length which will be absorbed by the organic polymer and not by the inorganic material.

A detector is indicated at 24 and is connected to a TV monitor 26. The monitor will show visually which parts have a coating which absorbs the non-visible light and which parts do not. This will allow a workman adjacent the conveyor and looking at a black/white monitor to quickly separate the parts having an inorganic coating from parts having an organic coating. Parts having an organic coating will appear white.

The invention should not be limited to non-visible light of a specific wave length. The type of light which is used, and the source which provides it, will be dependent on the types of coating which are applied to the products. What is important is to have light of a wave length which will be absorbed by one coating and not by the other.

Whereas the preferred form of the invention has been shown and described herein, it should be realized that there may be many modifications, substitutions and alterations thereto.

The embodiments of the invention in which an exclusive property or privilege is claimed are defined as follows:

1. A process for applying a coating to plumbing parts and then distinguishing plumbing parts of like size and shape, which are visually indistinguishable by the type of coating applied thereto, including the steps of: applying a coating which is essentially organic in composition to a first group of plumbing parts; applying a coating which is essentially inorganic in composition to a second group of plumbing parts; illuminating both the first group of plumbing parts and the second group of plumbing parts with a non-visible light operating at a frequency which will be absorbed by only one of the inorganic and organic coatings; and displaying the illuminated parts of the first and second groups, with parts having said only one coating which absorbs the non-visible light appearing differently than parts having the other coating which does not absorb the non-visible light.

2. The process of claim 1 wherein the parts are illuminated in an essentially enclosed environment.

3. The process of claim 1 wherein the non-visible light is absorbed by the essentially organic coating.

4. The process of claim 3 wherein the organic coating is essentially a polymer.

5. The process of claim 3 wherein the non-visible light has a wave length of approximately 200–300 nanometer.

6. The process of claim 3 wherein the non-visible light has a wave length of approximately 3 to 6 microns.

7. The process of claim 5 wherein the non-visible light is provided by a laser.

8. The process of claim 5 wherein the non-visible light is provided by a lamp having illumination in the ultraviolet spectrum.

9. The process of claim 1 wherein the inorganic coating is essentially a ceramic.

10. The process of claim 8 wherein the inorganic coating is essentially a zirconium carbo-nitride.

* * * * *